(12) United States Patent
Denda et al.

(10) Patent No.: US 8,247,382 B2
(45) Date of Patent: Aug. 21, 2012

(54) METHOD FOR INCREASING OXYTOCIN RELEASE IN THE EPIDERMIS

(75) Inventors: Sumiko Denda, Yokohama (JP); Mitsuhiro Denda, Yokohama (JP); Kazuyuki Ikeyama, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 167 days.

(21) Appl. No.: 12/616,908

(22) Filed: Nov. 12, 2009

(65) Prior Publication Data
US 2010/0130438 A1 May 27, 2010

Related U.S. Application Data

(60) Provisional application No. 61/113,773, filed on Nov. 12, 2008.

(51) Int. Cl.
*A01N 43/04* (2006.01)
*A61K 31/70* (2006.01)

(52) U.S. Cl. ............. 514/43; 514/45; 514/46; 514/49; 514/50

(58) Field of Classification Search .............. None
See application file for complete search history.

(56) References Cited

OTHER PUBLICATIONS

Burnstock TRENDS in Pharmacological Sciences (2006), vol. 27, pp. 166-176.*
Nakano et al. Eur. J. Physiol. (2001), vol. 442, pp. 57-63.*
Renaudeau et al. J. Anim. Sci. (2001), vol. 79, pp. 1540-1548.*
Li et al. Am. J. Physiol. Heart Circ. Physiol. (2002), vol. 283, pp. H2636-H2643.*

* cited by examiner

*Primary Examiner* — Patrick Lewis
(74) *Attorney, Agent, or Firm* — McDermott Will & Emery LLP (57) ABSTRACT

A method for increasing oxytocin release through direct action on the epidermal keratinocytes is provided. The method for increasing oxytocin release in the epidermis includes increasing the calcium ion concentration in the epidermal cells. In the method of the present invention, the increase of the calcium ion concentration in the epidermal cells may be achieved by physically stimulating the skin. The physical stimulation may be achieved by applying a heat stimulus and/or a massage. The increase of the calcium ion concentration in the epidermal cells may be achieved by stimulating the epidermal cells by at least one agent selected from the group consisting of ATP, UTP, 4 alpha-phorbol 12,13-didecanoate, and pharmaceutically acceptable salts thereof.

10 Claims, 5 Drawing Sheets

METHOD FOR INCREASING OXYTOCIN RELEASE IN THE EPIDERMIS

CROSS-REFERENCE TO PRIOR APPLICATIONS

Priority is claimed to U.S. Provisional Patent Application No. 61/113,773, filed on Nov. 12, 2008, the entire disclosure of which is hereby incorporated by reference herein.

FIELD

The present invention relates to a method for increasing oxytocin release in the epidermis, more specifically, to a method for increasing oxytocin release in the epidermis by massage.

BACKGROUND

Oxytocin is a peptide hormone which consists of nine amino acid residues. Oxytocin is known to be synthesized in nerve cells located in the paraventricular and supraoptic nuclei of hypothalamus, and released from the posterior pituitary into the blood. Known biological activities of oxytocin include uterine contraction and milk ejection activities. According to reports, intranasal administration of oxytocin increases trust in others (Kosfeld M. et al., Nature, 435: 673-676 (2005)), and decreases fears (Kirsch P. et al., J. Neurosci., 25: 11489-93 (2005)). In addition, animal and human studies revealed that oxytocin in the brain controls social behaviors including generating social recognition memory and nurturing behavior, and down-regulates stress responses including anxiety neurosis (Haruhiro Higashida, Protein, Nucleic Acid, Enzyme, 52: 1832-1839 (2007); and Neumann, I. D. Cell Metabolism, 5:231-233 (2007)). Thus, in addition to known biological activities, oxytocin is involved in higher mental functions required for the maintenance of human relationships and is considered to be effective in emotional improvement.

SUMMARY

As will be illustrated by examples, the present invention is based on new findings that oxytocin and mRNA encoding an oxytocin precursor are present in the skin, that the amount of oxytocin released from the skin increases upon skin stimulation, and that the amount of oxytocin released from the skin increases depending on the type of stimulation.

Oxytocin has conventionally been considered to be produced and released mainly in the central nervous system. However, it has been found that oxytocin is also produced in the skin, specifically in the upper layers of the epidermis. Therefore, there is a need to develop a method for increasing oxytocin release through direct action on epidermal keratinocytes.

The present invention provides a method for increasing oxytocin release in the epidermis, comprising increasing the calcium ion concentration in the epidermal cells.

In the method of the present invention, the increase of the calcium ion concentration in the epidermal cells may be achieved by physically stimulating the skin.

The physical stimulation may be achieved by applying a heat stimulus.

The physical stimulation may be achieved by simultaneously applying a heat stimulus and a massage.

In the method of the present invention, the increase of the calcium ion concentration in the epidermal cells may be achieved by stimulating the epidermal cells by at least one agent selected from the group consisting of ATP, UTP, 4alpha-phorbol 12,13-didecanoate, and pharmaceutically acceptable salts thereof.

Stimulating the epidermal cells by ATP may be achieved by delivering at least one agent selected from the group consisting of adenosine 5'-(3-thio)triphosphate, alpha, beta-methylene-ATP, and pharmaceutically acceptable salts thereof, to the epidermal cells.

The present invention provides a pharmaceutical preparation for increasing oxytocin release in the epidermis. The pharmaceutical preparation of the present invention comprises an agent for increasing the calcium ion concentration in the epidermal cells.

In the preparation of the present invention, the agent for increasing the calcium ion concentration in the epidermal cells may be at least one agent selected from the group consisting of adenosine 5'-(3-thio)triphosphate, alpha, beta-methylene-ATP, ATP, UTP, 4alpha-phorbol 12,13-didecanoate, and pharmaceutically acceptable salts thereof.

The preparation of the present invention may be applied to the skin surface.

The present invention provides a method for increasing oxytocin release in the epidermis, comprising simultaneously applying a massage and an agent for increasing the calcium ion concentration in the epidermal cells.

The present invention provides a method for increasing oxytocin release in the epidermis, comprising simultaneously applying a massage and at least one agent selected from the group consisting of adenosine 5'-(3-thio)triphosphate, alpha, beta-methylene-ATP, ATP, UTP, 4alpha-phorbol 12,13-didecanoate, and pharmaceutically acceptable salts thereof to the skin surface.

The present invention provides a method for increasing oxytocin release in the epidermis, comprising simultaneously applying a heat stimulus, a massage, and at least one agent selected from the group consisting of adenosine 5'-(3-thio) triphosphate, alpha, beta-methylene-ATP, ATP, UTP, 4alpha-phorbol 12,13-didecanoate, and pharmaceutically acceptable salts thereof to the skin surface.

The term "physical stimulation" as used herein refers to the application of pressure, heat, electricity or other physical stimulus. Stimulation with pressure comprises stimulation by pressing, rubbing, stroking, tapping, or kneading the skin. The stimulation with pressure may be achieved by applying a massage with a direct pressure to the skin either by human hands or feet or by a massager.

Massages relax and increase the comfort in mind and body, through the improvement of blood circulation, by loosening up the muscle strain, and thus, are popular among modern people living a stressful life. However, since the determination of whether it is comforting or discomforting is somewhat subjective, it is difficult to evaluate massage effects.

In order to develop a more effective and efficient massage method, the first thing to do is to establish an objective evaluation method for massage effects. The fact that the amount of oxytocin released from the skin can increase depending on the type of stimulation suggests that oxytocin is a potential index for the evaluation of massage effects.

As described above, intranasal administration of oxytocin increases trust in others and decreases fears. Therefore, oxytocin released upon skin stimulation may be directly related to the comfort, which is an effect of massages.

The "stimulation with heat", as used herein, is achieved by methods comprising, but not limited to, plastering a heating element on the skin or putting it in close contact with the skin, exposing the skin to the steam air or any other warm gas, and immersing a part of the body or limbs in warm water or any other warm liquid. Heat stimulation of tissues or cells in culture is commonly achieved by replacing the medium with another medium or buffer solution warmed under perfusion. For example, as explained by Chung M-K. et al., J. B. C. 278:32037-32046 (2003), the temperature is momentarily increased from 25° C. to 37° C. for a period of only 10 seconds, or slowly increased from 25° C. to 40° C. over a period of about 1 minute. In either case, the calcium ion concentration in the cultured epidermal cells increases.

Examples of the compound used in the examples of the present invention, which are known to increase the calcium ion concentration in the epidermal cells, include, but are not limited to, adenosine 5'-(3-thio)triphosphate, ATP, UTP, alpha, beta-methylene-ATP (Koizumi S. et al., Biochem. J. (2004) 380, 329-338), 4alpha-phorbol 12,13-didecanoate (Denda M. et al., J. Invest. Dermatol. (2007) 127: 654-659), and capsaicin as an agonist to the temperature-sensitive ion channel TRPV1 (Inoue K. et al., B. B. R. C. (2002) 291: 124-129).

As illustrated by the following examples, the present invention is based on the finding that oxytocin is present in the skin tissues, specifically in the cells from the upper layers of the epidermis to the stratum corneum. Accordingly, in the present specification, the skin tissue pieces isolated from the physically stimulated skin include at least the cells of the upper layer of the epidermis to the stratum corneum.

The amount of oxytocin released from the skin tissue pieces into the culture medium, as used herein, is calculated by subtracting the amount of oxytocin degraded in the culture medium and the amount of oxytocin adsorbed to or captured in the skin cells in culture from the sum of the amount of oxytocin produced in the skin cells before physical skin stimulation and released outside the cells in culture after the stimulation and the amount of oxytocin produced in the skin cells in culture and released outside the cells after the stimulation.

In the present invention, any culture condition may be used as long as oxytocin is released from the stimulated skin into the culture medium. The culture condition comprises culture period, temperature, and the like. The culture period is preferably long enough to cause oxytocin release from the skin into the culture medium. The culture condition may be at 37° C. for 24 hours.

In the present invention, a culture medium with any composition may be used on condition that it can be used to immerse and culture the skin tissue piece of the present invention isolated from the skin; that it will not hinder either the oxytocin production in the skin tissue pieces or oxytocin release to outside the cells; and that it will not kill the cells of the skin tissue pieces, to release intracellular protease into the culture medium and to degrade the oxytocin in the culture medium. However, the use of culture media supplemented with serum or pituitary extracts must be avoided, since they intrinsically contain oxytocin thereby affecting the quantification of oxytocin derived from the skin. Preferred culture medium may be Defined Keratinocyte-SFM (Invitrogen) or Epilife AOF Kit (Invitrogen).

In the present invention, the amount of oxytocin released into the culture medium may be determined by a method well known to those skilled in the art. For example, the determination may be made by purifying an oxytocin fraction from the culture medium by reversed phase chromatography or any other means, and by dissolving the fraction again in an appropriate buffer to concentrate the fraction and replace the solvent, followed by quantification with the ELISA method. The ELISA method may be carried out using, for example, Oxytocin EIA Kit (Assay Designs, Inc.). Alternatively, after the concentration of the fraction and replacement of the solvent, oxytocin is labeled with a fluorescent substance, and analyzed by HPLC to quantify the eluted peak of oxytocin.

DETAILED DESCRIPTION OF THE INVENTION

The present invention will be described in detail by the following examples, but the present invention will not be limited to these examples.

Example 1

1. Location of Oxytocin
1-1. Method

For immunohistochemical study, human skin sections (three voluntary donors, age: 55-66, female) and back skin sections of hairless mouse HR-1 ($Hr^{hr}/Hr^{hr}$) (7 weeks old, male) were frozen into blocks, and sliced into 6 μm thick tissue sections. The sections were fixed with methanol, and were stained with an anti-oxytocin antibody (Chemicon International) and a fluorescence-labeled secondary antibody (Invitrogen Japan K.K.), and the fluorescence images were acquired.

For molecular genetic study, mRNA of an oxytocin precursor was detected by the RT-PCR method. The PCR templates were cDNA prepared from epidermal keratinocytes of human neonates (Kurabo Industries Ltd.), and cDNA from human skin (BioChain Inc.). As the positive control for the PCR reaction, cDNA from human brain (Clontech Co., Ltd) was used for the template. Table 1 shows the primer sequences used for the amplification of oxytocin cDNA. The nucleotide sequences a, b, c, and d in Table 1 were subjected to PCR reaction using, for example, Phusion DNA polymerase (NEB) in accordance with the protocol attached herewith. The PCR products were electrophoresed together with a molecular weight marker (100 bp ladder, Toyobo Co., Ltd.) on an agarose gel, and fluorescence images of the bands stained with ethidium bromide were obtained.

TABLE 1

| PCR Primers used to detect human oxytocin mRNA | | | |
|---|---|---|---|
| Primer name | Position * | Sequence | PCR product length |
| a | 89-108 | ccgcctgctacatccagaac | 390 bp |
| b | 478-459 | atttctggggtggctatggg | |

TABLE 1-continued

PCR Primers used to detect human oxytocin mRNA

| Primer name | Position * | Sequence | PCR product length |
|---|---|---|---|
| c | 217-236 | gaagagctgggctgcttcgt | 201 bp |
| d | 417-397 | gtttcagcgctgggagaaggt | |

* Position indicates the number from the 5' end of human oxytocin prepropeptide mRNA (Genbank No. NM000915).

1-2. Result

Figure 1:
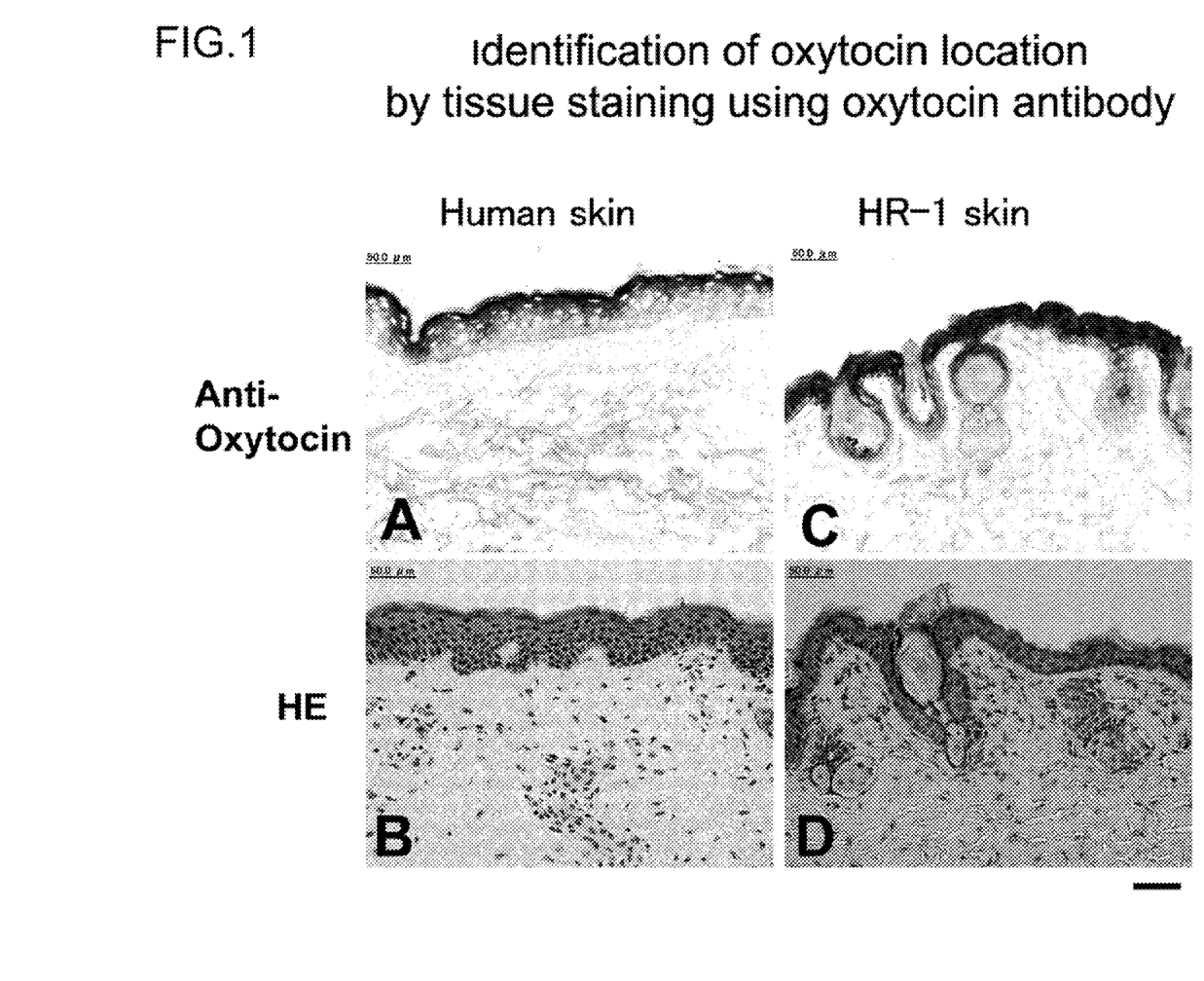
FIG. 1 shows micrographs of stained skin tissues of a human face and an HR-1 mouse.

FIG. 1 shows micrographs of skin tissue sections of human face (FIGS. 1A and 1B), and hairless mouse HR-1 strain (FIGS. 1C and 1D); FIGS. 1A and 1C show the immunohistochemical staining patterns of the specimens stained using the anti-oxytocin antibody, and FIGS. 1B and 1D show the adjacent tissue sections stained with hematoxylin and eosin. In FIGS. 1A and 1C, sites reacted with the oxytocin antibody are indicated in black color. FIGS. 1B and 1D represent the state of tissue construction. These results indicate that, in both the human and mouse, oxytocin is present in the skin, specifically in the region from the upper layers of the epidermis to the stratum corneum.

Figure 2:
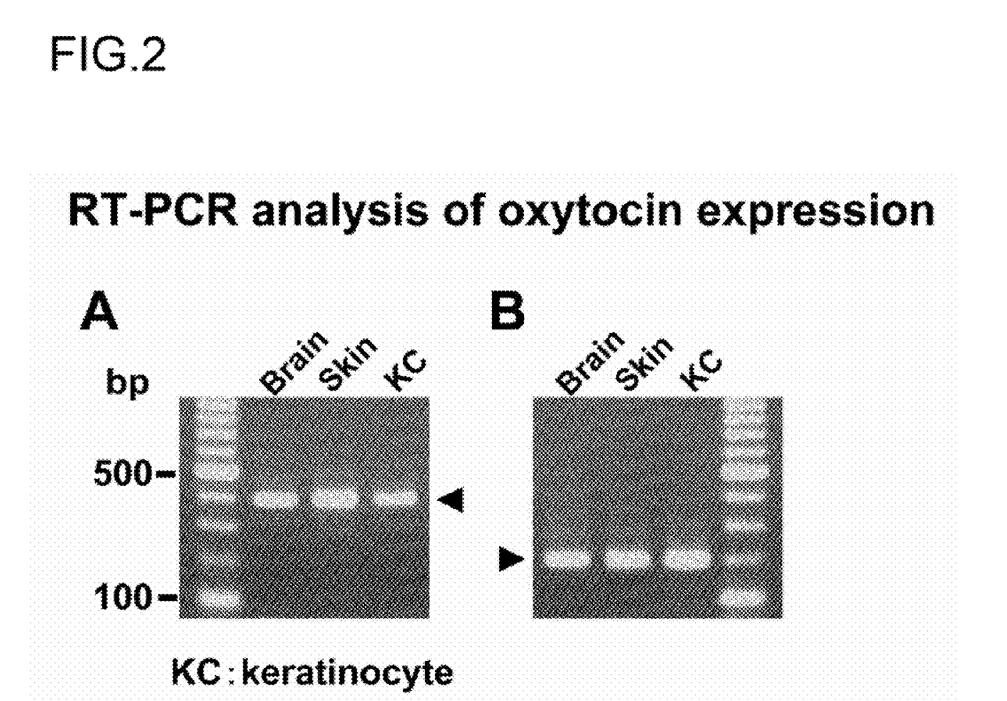
FIG. 2 shows photographs of the results of agarose gel electrophoresis for the detection of oxytocin mRNA by RT-PCR.

FIG. 2 shows the results of RT-PCR of human skin and cultured keratinocytes. FIG. 2A shows the result of PCR of primers a and b, indicating the detection of 390 bp DNA fragments as expected. FIG. 2B shows the result of Nested PCR carried out for the confirmation of the internal sequence of the DNA amplified by the PCR of FIG. 2A. PCR was carried out using primers c and d, and a portion of the PCR reaction solution of FIG. 2A as the template. As a result of this, 201 bp DNA fragments were detected as expected. The combination of the primers used herein was designed to anneal to positions flanking an intron on the genomic DNA. The lengths of the detected bands met expectations, suggesting that the amplified cDNAs are not derived from genome but from mRNA. More specifically, it has been revealed that the mRNA of an oxytocin precursor is expressed in the human skin and cultured keratinocytes as well as in the brain.

Example 2

2. Oxytocin Production by Keratinocytes 2-1. Method (Influence of ATP Gamma S Addition)

The keratinocytes used herein were epidermal keratinocytes of human neonates up to a passage number of 4 (Kurabo Industries Ltd.). The culture medium was Defined Keratinocyte-SFM (Invitrogen Japan K.K.). The keratinocytes were grown to confluence in 10-cm dishes at 37° C. for several days with the culture medium replaced on alternate days, and then the calcium chloride concentration in the culture medium was increased to 1.8 mM thereby inducing differentiation. After a lapse of 45 hours, adenosine-5'-(3-thio)triphosphoric acid tetralithium salt (Sigma Co., hereinafter referred to as "ATP gamma s-Li") was added to each dish so as to make the final concentrations of 0, 10, 30, 100, and 300 µM, and the incubation of culture was continued at 37° C. The culture medium was collected 10 minutes after the addition of ATP gamma s, and the amount of oxytocin was measured with the ELISA method.

Determination of Oxytocin by ELISA Method

Oxytocin in the collected culture medium was purified and concentrated using a reversed phase column (C18 Sep-pak Light, Waters Co.), and eluted with an aqueous solution containing 60% acetonitrile and 0.1% trifluoroacetic acid. More specifically, the column eluate fraction containing oxytocin was freeze-dried, and dissolved again in a small amount of buffer solution (included in the EIA kit), and the oxytocin in the culture medium was concentrated at least 20 fold. Thereafter, the oxytocin concentration in the concentrated oxytocin solution was measured by the competitive ELISA method using Oxytocin EIA Kit (Assay Designs, Inc). The measurement procedure described in the instruction manual attached to the kit was followed. Briefly, a sample containing oxytocin was mixed with oxytocin conjugated with alkaline phosphatase, and then bound to a rabbit anti-oxytocin antibody. Subsequently, the anti-oxytocin antibody in the above mixture was bound to a goat anti-rabbit IgG immobilized in each well of a 96-multiwell plate As a control test, a known amount of oxytocin was used in place of the sample, and mixed with oxytocin conjugated with alkaline phosphatase. The absorbance of the color reaction by alkaline phosphatase was measured, and a semilogarithmic standard curve was generated by plotting the absorbance change due to the competitive inhibition against the known amount of oxytocin. The standard curve was used to determine the amount of oxytocin corresponding to the absorbance of the sample.

(Influence of EGTA Addition)

The procedure same as the above described was carried out, except that 0 and 2 mM ethylene glycol bis(2-aminoethyl ether) tetraacetic acid (hereinafter referred to as EGTA, Wako Pure Chemical Industries, Ltd.) was further added to the culture medium. EGTA was added 5 minutes before the addition of ATP gamma s.

2-2. Result

Figure 3:
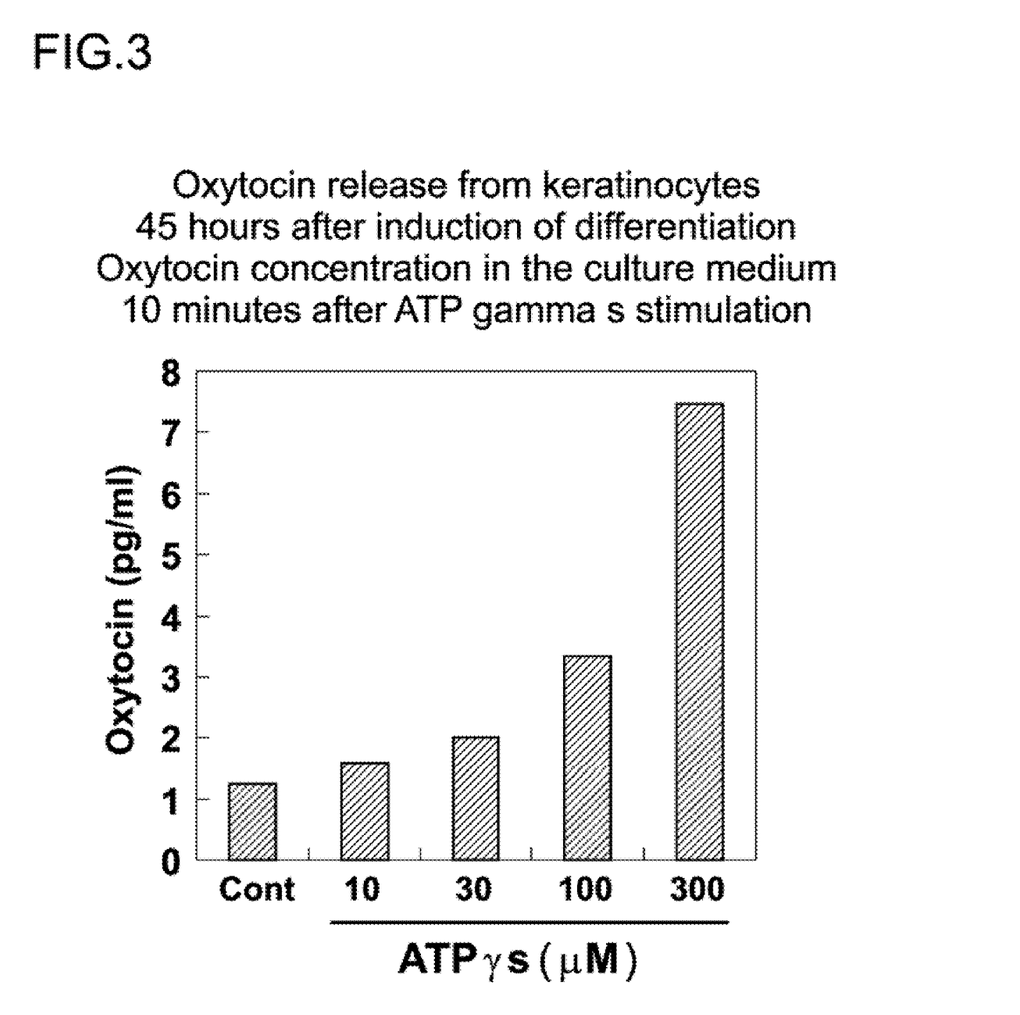
FIG. 3 is a graph showing the oxytocin concentrations in the culture media after culture at different concentrations of ATP gamma s added.

FIG. 3 is a bar graph showing the oxytocin concentrations in the culture media after incubation at different concentrations of ATP gamma s added. The oxytocin concentration was about 1 pg/mL in the culture medium containing no ATP gamma s. The oxytocin concentration increased with increases of ATP gamma s, and exceeded 7 pg/mL when the amount of ATP gamma s was 300 µM.

Figure 4:
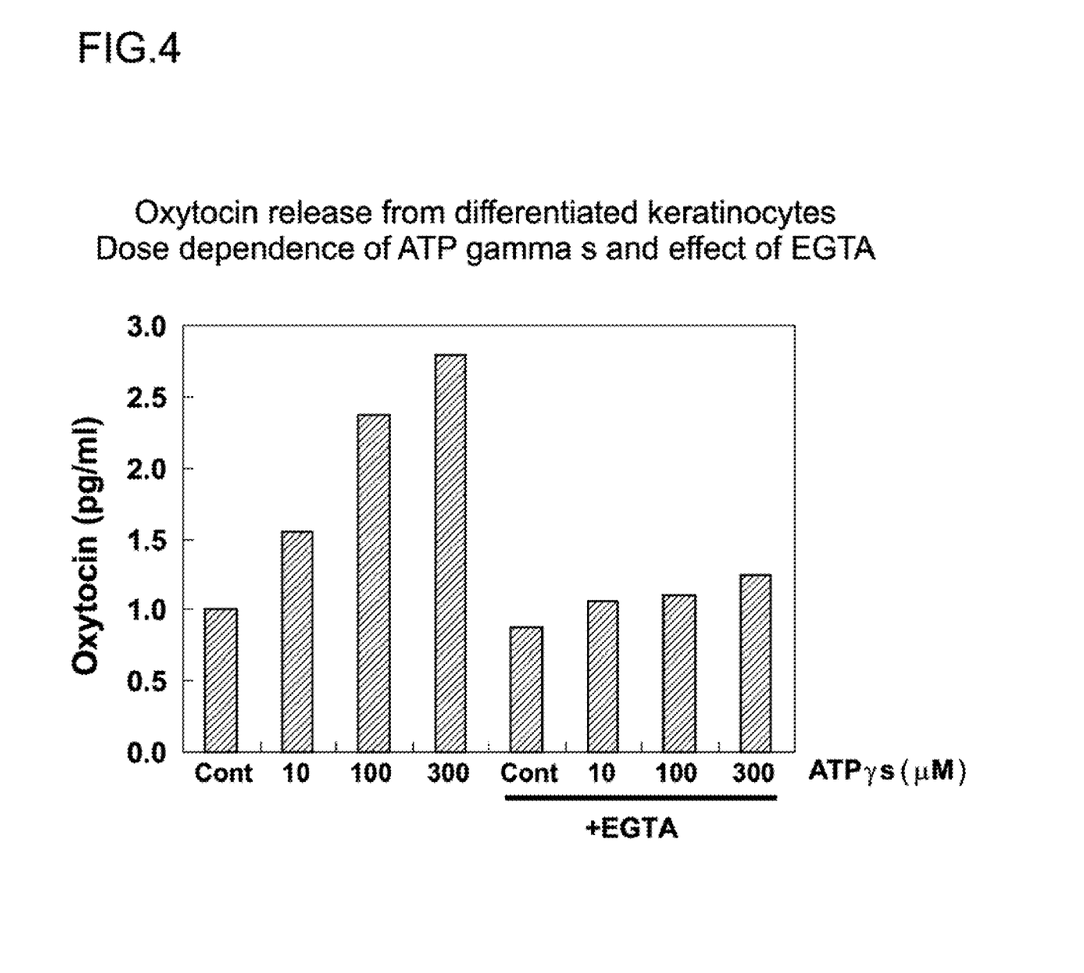
FIG. 4 is a graph showing the oxytocin concentrations in the culture media containing or free of 2 mM EGTA after culture at different concentrations of ATP gamma s added.

FIG. 4 is a bar graph showing the oxytocin concentrations in the culture media containing 2 mM EGTA after incubation at different concentrations of ATP gamma s added. The increase of the oxytocin concentration with increases of ATP gamma s was inhibited under conditions where EGTA is contained.

ATP gamma s is a persistent derivative of ATP, and acts on ATP receptors (P2X, P2Y) in the same manner as ATP. It is known that ATP and ATP gamma s added to keratinocytes increase the $Ca^{2+}$ concentration in the keratinocytes in a concentration-dependent manner (J. Clin. Invest. (1992) 90, 42-51; Biochem. J. (2004) 380, 329-338). EGTA is a chelating agent having high affinity for $Ca^{2+}$. In the present example, it is considered that EGTA added to the culture medium captures $Ca^{2+}$ in the culture medium, and thus the $Ca^{2+}$ concentration in the culture medium is considered to be extremely low. The results shown in FIGS. 3 and 4 suggest that the addition of ATP gamma s to keratinocytes causes the $Ca^{2+}$ influx into the cytoplasm of keratinocytes through ion channels in the cell membranes such as P2X receptors, thereby increasing the $Ca^{2+}$ concentration in the cells to promote the release of oxytocin. Accordingly, keratinocytes are considered to release oxytocin through the increase of intracellular $Ca^{2+}$.

Example 3

3. Production and Release of Oxytocin in Massaged Skin Ex Vivo

3-1. Method

Hairless mice HR-1 ($Hr^{hr}/Hr^{hr}$, 14 weeks old, male) were used for the study. In order to prepare samples to be subjected to a massage, the back skin was removed and cut into pieces of 1.5 cm×2.5 cm, then were placed on Teflon meshes, and floated on culture dishes each containing a culture medium MCDB153 (Sigma Co.). After the pieces were cultured in an incubator at 37° C. for 3 hours, an urethane rubber sheet was placed on the stratum corneum of each skin tissue piece, and a columnar weight (diameter 2 cm, height 2 cm, weight 53 g) was placed on the sheet. The samples were mechanically stimulated as follows. The weight was placed on the urethane rubber sheet with its curved surface downward, the culture dish was placed on a seesaw shaker (23.5 cycles/minute), and the weight was continually rolled for 1 hour, thereby making a sample of the Rolling group. Aside from this, the weight was placed on the urethane rubber sheet with its bottom downward, and were left to stand thereon for 1 hour, thereby making a sample of the Press group. In addition, a sample of the Control group was made by allowing the sample to stand for the same period with nothing placed on the urethane rubber sheet. After the stimulation, the urethane rubber sheet was removed, and each skin piece was floated on 1.25 mL of new culture medium, and cultured at 37° C. for 24 hours. Thereafter, the culture media were collected, and the oxytocin amount was measured by the ELISA method in the same manner as in Example 2.

3-2. Result

Figure 5:
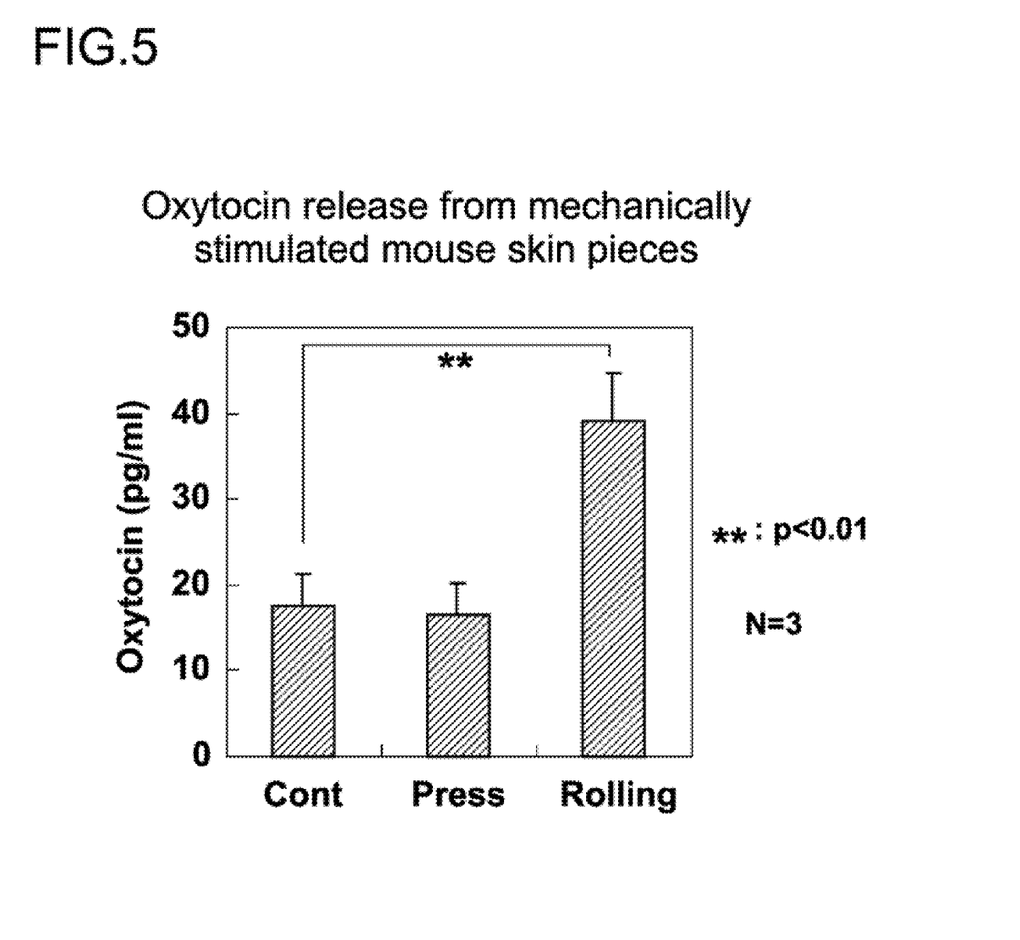
FIG. 5 is a graph showing the result of analysis of oxytocin collected from the skin culture media after mechanical stimulation (pressing and rolling).

FIG. 5 is a bar graph showing the oxytocin concentration in the skin culture media of the Rolling, Press, and Control groups. The heights of the bars represent the average amounts of oxytocin released from three skin tissue pieces of each group. The error bars represent the standard deviations of the three pieces. The average oxytocin concentration of the Control group was less than 20 pg/mL, which was equivalent to that of the Press group. On the other hand, the average oxytocin concentration of the Rolling group was about 40 pg/mL, which was about twice as much as the Control group. Student's t-test was done between the Control group and the Rolling group; the risk factor was calculated at $p<0.01$ (Cont vs Rolling: p=0.0050; Cont vs Press: p=0.7186; Press vs Rolling; p=0.0044), indicating that the increase of the oxytocin concentration in the Rolling group was statistically significant in comparison with that in the Control group. The result has revealed that the amount of oxytocin released from the skin is increased by physical stimulation such as a massage, and suggests that the production of oxytocin in the skin may be increased by a massage.

What is claimed is:

1. A method for increasing oxytocin release from epidermal cells, comprising increasing calcium ion concentration in the epidermal cells.

2. The method of claim 1 wherein the epidermal cells are in a culture medium.

3. The method of claim 1 or 2, wherein increasing the calcium ion concentration in the epidermal cells comprises physically stimulating the epidermal cells.

4. The method of claim 3 or 2, wherein the physical stimulation is achieved by applying a heat stimulus.

5. The method of claim 3 or 2, wherein the physical stimulation is achieved by simultaneously applying a heat stimulus and a massage.

6. The method of claim 1, wherein the increase of the calcium ion concentration in the epidermal cells is achieved by stimulating the epidermal cells by delivering to the epidermal cells at least one agent selected from the group consisting of ATP, UTP, 4alpha-phorbol 12,13-didecanoate, and pharmaceutically acceptable salts thereof.

7. The method of claim 6, wherein stimulating the epidermal cells by ATP is achieved by delivery to the epidermal cells of at least one agent selected from the group consisting of adenosine 5'-(3-thio)triphosphate, alpha, beta-methylene-ATP, and pharmaceutically acceptable salts thereof.

8. A method for increasing oxytocin release in the epidermis, comprising simultaneously applying a massage and an agent for increasing calcium ion concentration in epidermal cells to a skin surface.

9. A method for increasing oxytocin release in the epidermis, comprising simultaneously applying a massage and at least one agent selected from the group consisting of adenosine 5'-(3-thio)triphosphate, alpha, beta-methylene-ATP, ATP, UTP, 4alpha-phorbol 12,13-didecanoate, and pharmaceutically acceptable salts thereof to a skin surface.

10. A method for increasing oxytocin release in the epidermis, comprising simultaneously applying a heat stimulus, a massage, and at least one agent selected from the group consisting of adenosine 5'-(3-thio)triphosphate, alpha, beta-methylene-ATP, ATP, UTP, 4alpha-phorbol 12,13-didecanoate, and pharmaceutically acceptable salts thereof to a skin surface.

* * * * *

```
SEQUENCE LISTING

<160> NUMBER OF SEQ ID NOS: 4

<210> SEQ ID NO 1
<211> LENGTH: 20
<212> TYPE: DNA
<213> ORGANISM: Homo sapiens
<220> FEATURE:
<221> NAME/KEY: misc_feature
<223> OTHER INFORMATION: human oxytocin prepropeptide mRNA forward
      primer

<400> SEQUENCE: 1
ccgcctgcta catccagaac                                                   20

<210> SEQ ID NO 2
<211> LENGTH: 20
<212> TYPE: DNA
<213> ORGANISM: Homo sapiens
<220> FEATURE:
<221> NAME/KEY: misc_feature
<223> OTHER INFORMATION: human oxytocin prepropeptide mRNA reverse
      primer

<400> SEQUENCE: 2
atttctgggg tggctatggg                                                   20

<210> SEQ ID NO 3
<211> LENGTH: 20
<212> TYPE: DNA
<213> ORGANISM: Homo sapiens
<220> FEATURE:
<221> NAME/KEY: misc_feature
<223> OTHER INFORMATION: human oxytocin prepropeptide mRNA forward
      primer

<400> SEQUENCE: 3
gaagagctgg gctgcttcgt                                                   20
```

```
<210> SEQ ID NO 4
<211> LENGTH: 21
<212> TYPE: DNA
<213> ORGANISM: Homo sapiens
<220> FEATURE:
<221> NAME/KEY: misc_feature
<223> OTHER INFORMATION: human oxytocin prepropeptide mRNA reverse
      primer

<400> SEQUENCE: 4
gtttcagcgc tgggagaagg t                                              21
```